(12) United States Patent
Hollopeter et al.

(10) Patent No.: US 10,321,970 B1
(45) Date of Patent: Jun. 18, 2019

(54) HANDLE ASSEMBLY FOR A SURGICAL LIGHTING SYSTEM

(71) Applicant: American Sterilizer Company, Mentor, OH (US)

(72) Inventors: Michael Hollopeter, Kirtland, OH (US); Lance Clark Bellows, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 15/865,333

(22) Filed: Jan. 9, 2018

(51) Int. Cl.
| A45C 13/26 | (2006.01) |
| A61B 90/00 | (2016.01) |
| A61B 34/00 | (2016.01) |
| A61B 17/00 | (2006.01) |
| A61B 46/10 | (2016.01) |

(52) U.S. Cl.
CPC .............. *A61B 90/36* (2016.02); *A61B 34/76* (2016.02); *A61B 34/74* (2016.02); *A61B 46/10* (2016.02); *A61B 2017/0046* (2013.01)

(58) Field of Classification Search
CPC ..... Y10T 16/466; Y10T 16/469; Y10T 16/44; A61B 90/30; A61B 90/36; A61B 90/361; A61B 34/74; A61B 34/76; A61B 46/10; A61B 2017/0046; A61B 2017/00464; A61B 2090/308; B25G 3/04; B25G 3/12; B25G 3/24
See application file for complete search history.

(56) References Cited

U.S. PATENT DOCUMENTS

| 4,316,237 | A |  | 2/1982 | Yamada et al. |
| 4,621,735 | A |  | 11/1986 | Coon et al. |
| 4,844,252 | A |  | 7/1989 | Barron et al. |
| 4,878,156 | A |  | 10/1989 | Hallings et al. |
| 4,885,443 | A | * | 12/1989 | Simcoe ............... H01H 13/023 200/296 |
| 5,188,454 | A | * | 2/1993 | Quintanilla ........... F21V 21/403 362/376 |
| 5,233,271 | A |  | 8/1993 | Huang et al. |
| 5,561,278 | A | * | 10/1996 | Rutten ................ H01H 13/702 200/5 A |
| 6,370,735 | B1 |  | 4/2002 | Horan et al. |
| 6,402,351 | B1 |  | 6/2002 | Borders et al. |
| 6,633,328 | B1 | * | 10/2003 | Byrd ..................... H04N 7/183 348/143 |
| 6,692,141 | B2 |  | 2/2004 | Jesurun et al. |
| 6,715,904 | B2 |  | 4/2004 | Naughton |
| 6,863,422 | B2 |  | 3/2005 | Jesurun et al. |
| 6,909,465 | B2 | * | 6/2005 | Liang ................... H04N 3/1575 348/143 |

(Continued)

OTHER PUBLICATIONS

Specialty Disposable Light Handle for use with Trumpf Medical™ ALC Plus Surgical Light product brochure, Hill-Rom, Feb. 27, 2015, pp. 1-2.

(Continued)

*Primary Examiner* — Chuck Y Mah
(74) *Attorney, Agent, or Firm* — Kusner & Jaffe

(57) ABSTRACT

A handle assembly comprised of a base and a detachable handle that mounts to the base. The base includes integrated electronics, such as switches. The detachable handle includes buttons for activating the switches.

12 Claims, 9 Drawing Sheets

(56) References Cited

U.S. PATENT DOCUMENTS

| | | | |
|---|---|---|---|
| 7,144,035 B2 * | 12/2006 | Min | B60Q 5/003 |
| | | | 280/731 |
| 7,285,741 B2 * | 10/2007 | Kato | H01H 13/705 |
| | | | 200/341 |
| 7,441,923 B2 | 10/2008 | Hünerbein et al. | |
| 8,789,243 B2 | 7/2014 | Denmark | |
| 8,833,953 B2 | 9/2014 | Schmid et al. | |
| 2003/0210559 A1 | 11/2003 | Jesurun et al. | |
| 2011/0300505 A1 | 12/2011 | Jessop et al. | |
| 2016/0192990 A1 * | 7/2016 | Wang | A61B 18/148 |
| | | | 606/37 |

OTHER PUBLICATIONS

HarmonyAIR® M-Series Surgical Lighting System product brochure, STERIS Corporation, Apr. 2016, pp. 1-8.
FREES® Camera System product brochure, STERIS Corporation, Apr. 2017, pp. 1-4.
iLED™ 7 Surgical Light product brochure, Trumpf Medical, Hill-Rom, Jan. 9, 2017, pp. 1-8.

\* cited by examiner

HANDLE ASSEMBLY FOR A SURGICAL LIGHTING SYSTEM

FIELD OF THE INVENTION

The present invention relates generally to a handle assembly for a lighting system, and more particularly to a handle assembly having a detachable handle that mounts to a base with integrated electronics.

BACKGROUND OF THE INVENTION

Some existing surgical lighting systems include lightheads having a permanently mounted control handle that requires the use of a sterile cover or sterilizable handle cover adapter in order to maintain a sterile field. The control handle has integrated capacitive sensors that replace conventional replace mechanical control buttons. These capacitive sensors are susceptible to unintended activation during positioning of the lighthead. Furthermore, there is no tactile feedback associated with activation of the capacitive sensors, thereby making them difficult to use.

Alternatives to a permanently mounted control handle include a reusable detachable control handle which can be repeatedly sterilized or a sterile disposable detachable control handle. However, existing prior art detachable control handles do not provide means for activating lighting system controls that provide tactile feedback and are not susceptible to unintended activation during positioning of the lighthead.

The present invention provides a handle assembly for a lighting system that overcomes these and other drawbacks of the prior art.

SUMMARY OF THE INVENTION

In accordance with the present invention, there is provided a handle assembly for a lighting system, comprising: a base having at least one contact element mounted thereto, each contact element having at least one switch; and a detachable handle mountable to the base, the handle having a button membrane that includes at least one button element for respectively engaging with the at least one contact element.

An advantage of the present invention is the provision of a handle assembly for a surgical lighting system that includes a reusable, sterilizable detachable handle.

Another advantage of the present invention is the provision of a handle assembly for a surgical lighting system that eliminates the requirement to use a disposable handle cover to maintain sterility.

A still further advantage of the present invention is the provision of a handle assembly for a surgical lighting system that has buttons which provide tactile feedback to the user.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, embodiments of which will be described in detail in the specification and illustrated in the accompanying drawings which form a part hereof, and wherein.

DETAILED DESCRIPTION OF THE INVENTION

Figure 1:
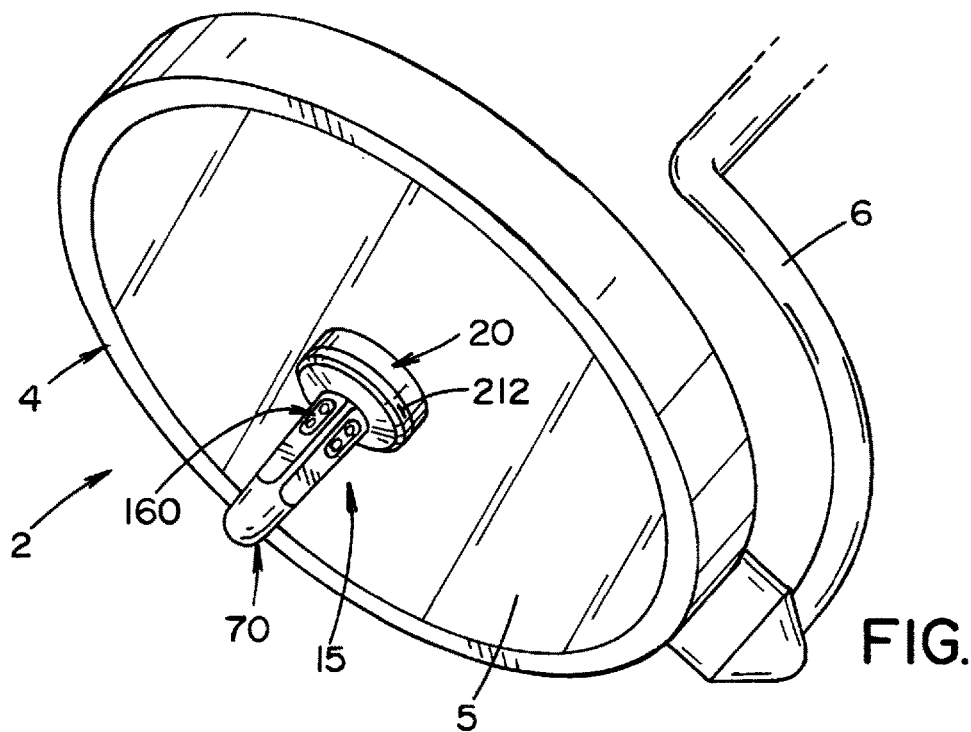
FIG. 1 is a perspective view of a lighting system including a handle assembly according to an embodiment of the present invention.
Figure 2:
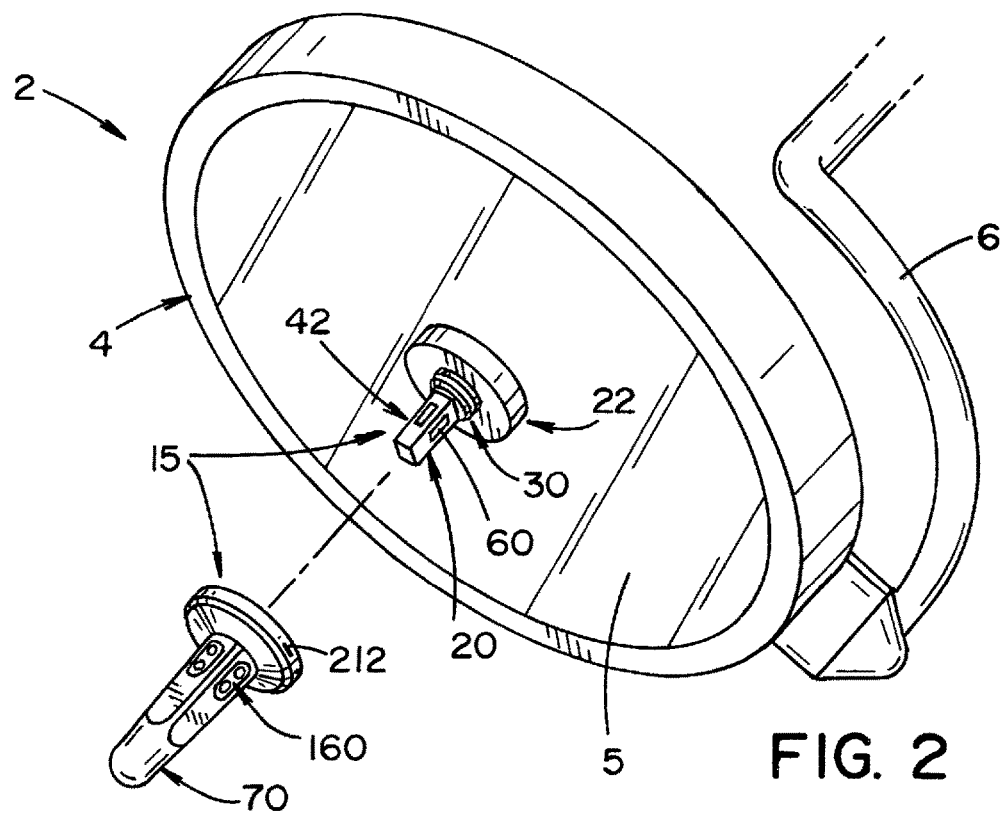
FIG. 2 shows the lighting system of FIG. 1 with an exploded view of the handle assembly comprised of a base and a detachable handle.
Figure 3:
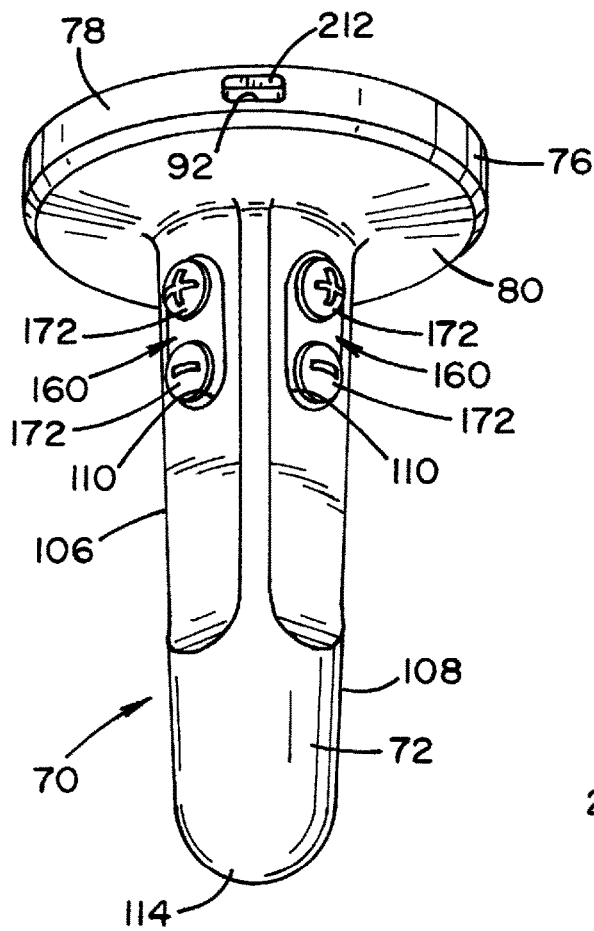
FIG. 3 is a first perspective view of the detachable handle.

Referring now to the drawings wherein the showings are for the purposes of illustrating embodiments of the invention only and not for the purposes of limiting same, FIGS. 1 and 2 show a perspective view of a portion of a lighting system 2 that includes a lighthead 4 mounted to a support member 6. Lighthead 4 is comprised of a lighting unit 5, a control unit (not shown), and a handle assembly 15 according to an embodiment of the present invention. Lighting unit 5 includes a plurality of lighting elements, such as LEDs. The control unit includes a microcontroller and associated control electronics. Handle assembly 15 is comprised of a base 20 and a detachable handle 70, which are described in detail below.

Detachable handle 70 is generally comprised of an outer housing 72 (best seen in FIGS. 3-10), an inner shell 130 (best seen in FIGS. 8-11), a plurality of button membranes 160 (best seen in FIGS. 8-11), a locking member 190 (best seen in FIGS. 8-10 and 12), and a retaining ring 230 (best seen in FIGS. 4 and 8-10).

Figure 9:
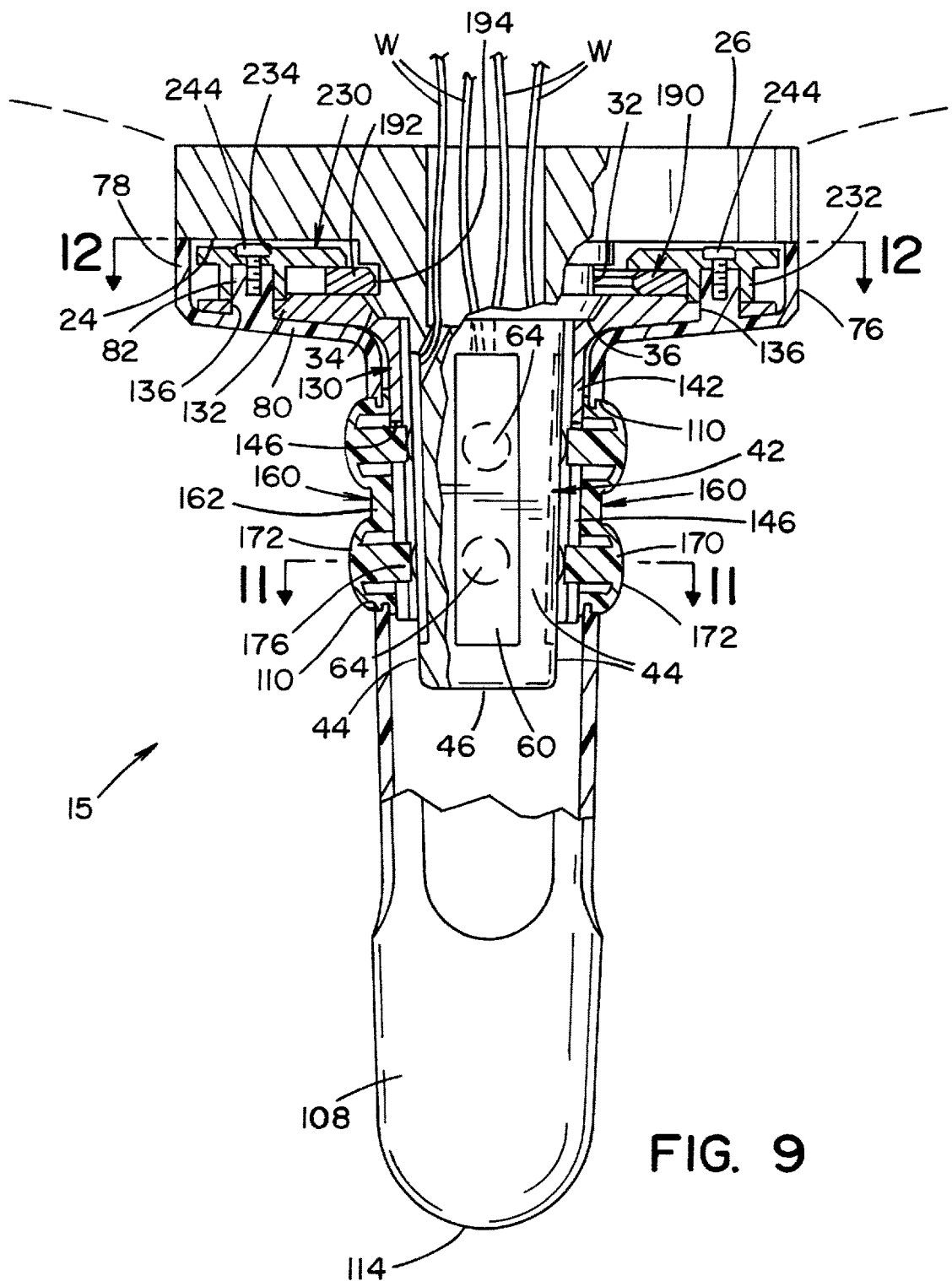
FIG. 9 is a partial sectional view of the handle assembly, with the detachable handle mounted to the base.
Figure 10:
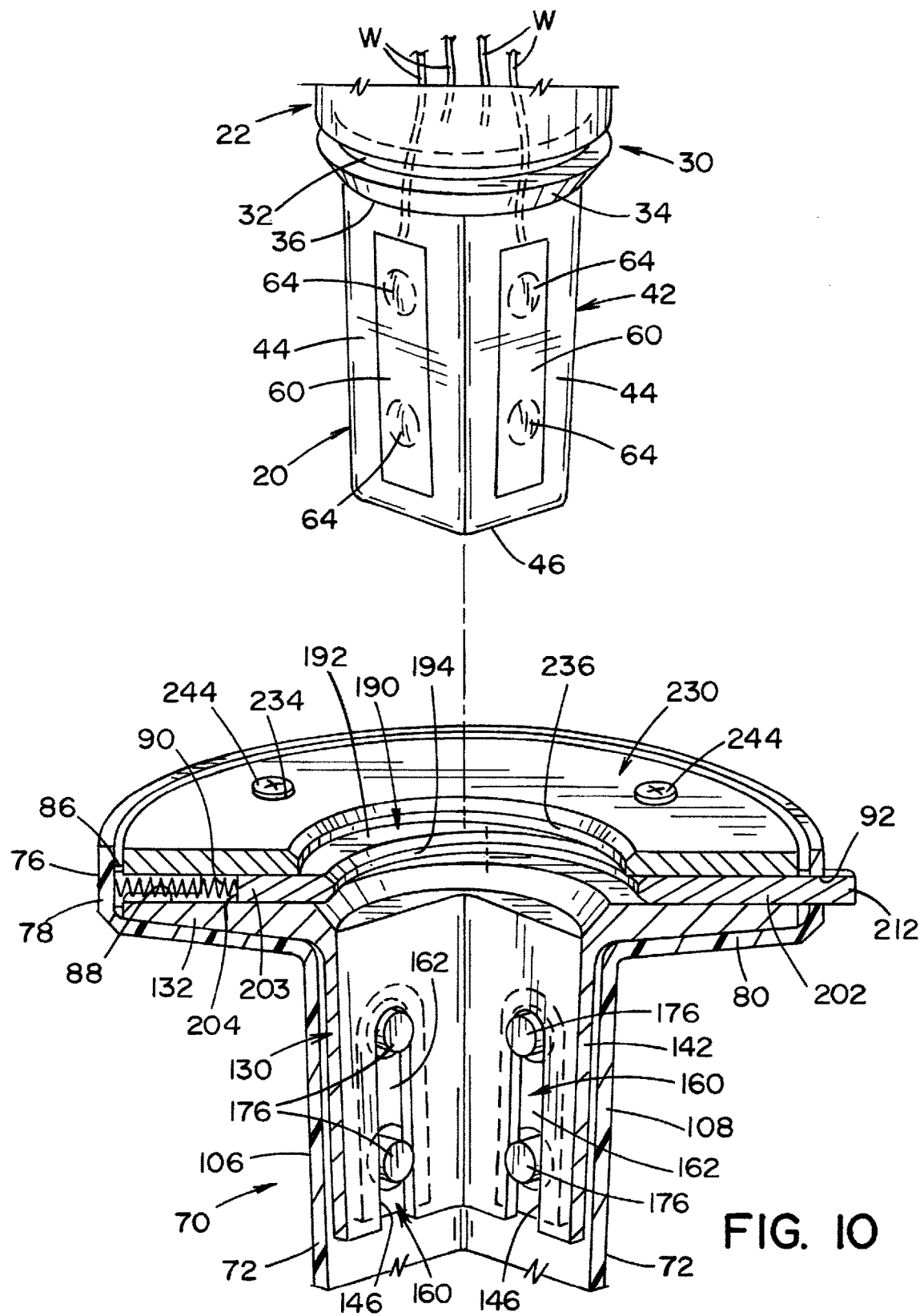
FIG. 10 is a partial exploded view of the handle assembly, with a sectional view of the detachable handle.
Figure 11:
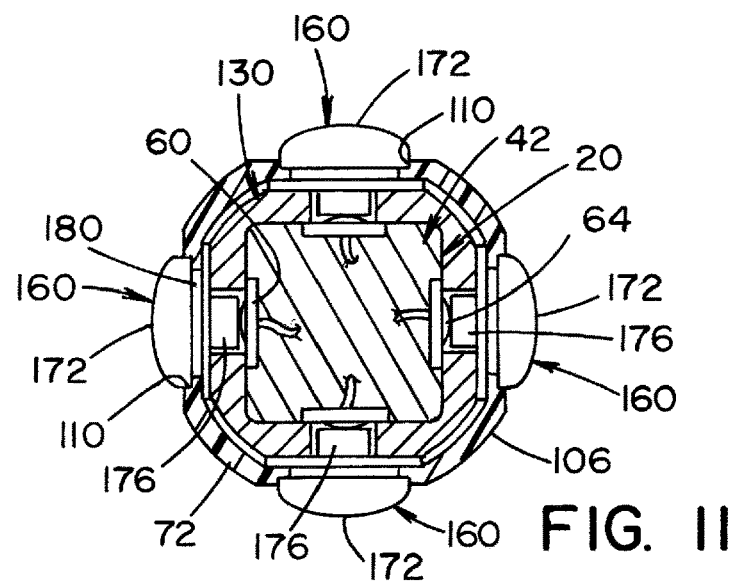
FIG. 11 is a cross-sectional view taken along lines 11-11 of FIG. 9.
Figure 12:
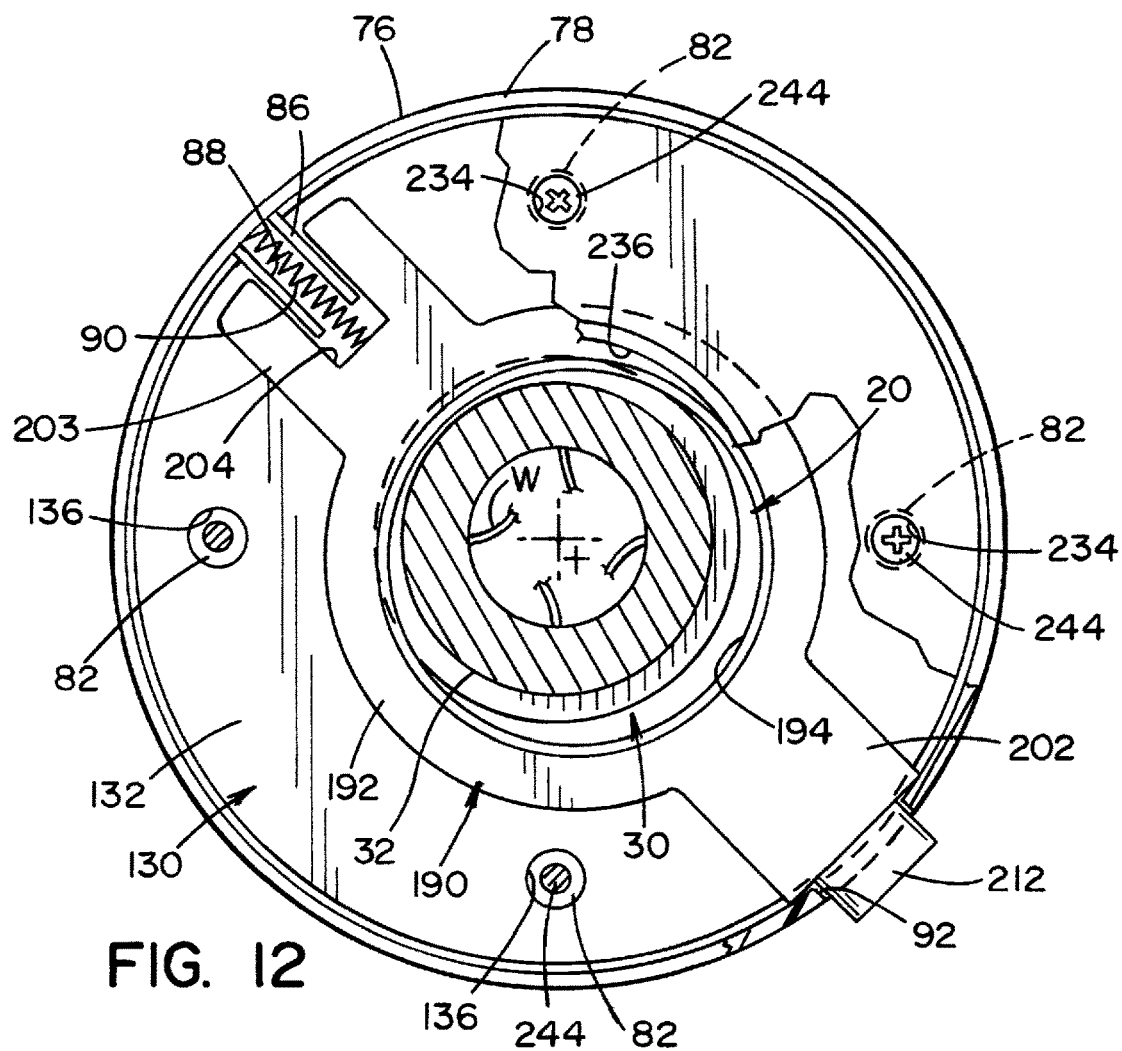
FIG. 12 is a cross-sectional view taken along lines 12-12 of FIG. 9.

Outer housing 72 includes a head portion 76 and a body portion 106. Head portion 76 has a side wall 78 and a bottom wall 80. Side wall 78 and bottom wall 80 define a generally cylindrical recess dimensioned to receive a portion of inner shell 130, locking member 190, and retaining ring 230, which are described in detail below. A plurality of mounting bosses 82 project from bottom wall 80, as shown in FIG. 9. Each mounting boss 82 includes an internal threaded recess dimensioned to receive a fastener 244 (e.g., a threaded screw). A locating tab 86 projects inward from side wall 78, as shown in FIG. 12. Locating tab 86 includes a channel 88 which is dimensioned to receive a bias member 90. In the illustrated embodiment, bias member 90 takes the form of a compression spring. An opening 92 is formed in side wall 78 of head portion 76, as best seen in FIGS. 10 and 12. Opening 92 is dimensioned to receive a release button 212 (of locking member 190), which extends through opening 92.

Body portion 106 of outer housing 72 includes a tubular-shaped side wall 108 and a bottom wall 114 at a distal end of outer housing 72. Openings 110 are formed in side wall 108 and are dimensioned to receive a portion of button membrane 160, as will be described below. Side wall 108 defines a recess dimensioned to receive a portion of inner shell 130, as best seen in FIGS. 8-10.

Figure 8:
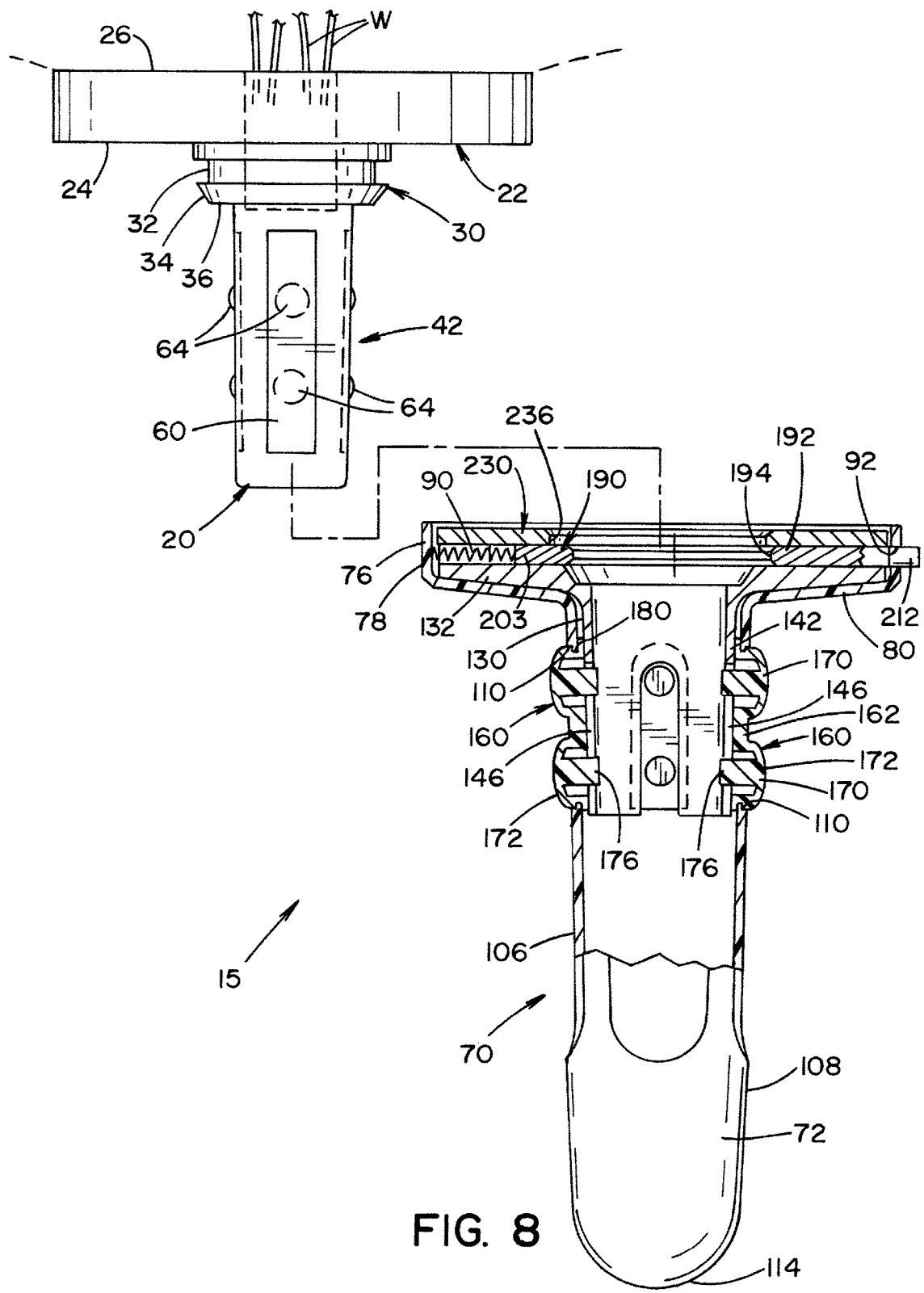
FIG. 8 is an exploded view of the handle assembly, with a partial sectional view of the detachable handle.

Inner shell 130 has a head portion 132 and a body portion 142, as best seen in FIGS. 8-10. In the illustrated embodiment, head portion 132 is a ring-shaped structure having a plurality of openings 136 formed therein, as shown in FIG. 9. Openings 136 are dimensioned to receive mounting bosses 82 of outer housing 72. Body portion 142 is a tubular-shaped structure having a plurality of slots 146. Slots 146 are dimensioned to receive a portion of button membrane 160, as best seen in FIGS. 8-10.

In the illustrated embodiment, each button membrane 160 has a body 162 and a plurality of button elements 170, as best seen in FIGS. 8-10. Each button element 170 includes an outward extending contact portion 172 that takes the form of a tactile domed button and an inward extending engagement portion 176 that takes the form of a plunger member. Contact portion 172 extends forward through opening 110 of outer housing 72, as best seen in FIG. 8. Engagement portion 176 extends through openings 110 of outer housing 72. Engagement portion 176 is dimensioned to be engageable with contact elements of base 20 when contact portion 172 is depressed by a user. A gap 180 is provided between body 162 and button elements 170 to capture an edge portion of side wall 108 of outer housing 72 adjacent to openings 110. In the illustrated embodiment, button membrane 160 is formed of silicone rubber. It is contemplated that a lighting element (e.g., one or more LEDs) may be located within detachable handle 70 to illuminate button membrane 160. In an embodiment of the present invention, button elements 170 may be used for user control of lighting unit 5, including, but not limited to, light intensity, ON/OFF, and the like.

Locking member 190 is generally comprised of a ring section 192 having a center opening 194, and projections 202 and 203, as best seen in FIG. 12. Projection 203 includes a slot 204 dimensioned to receive locating tab 86 of outer housing 72. Bias member 90 is located within the space defined by side wall 78, locating tab 86, and projection 203. Release button 212 extends outward from projection 202. As indicated above, release button 212 extends through opening 92 of outer housing 72.

Figure 4:
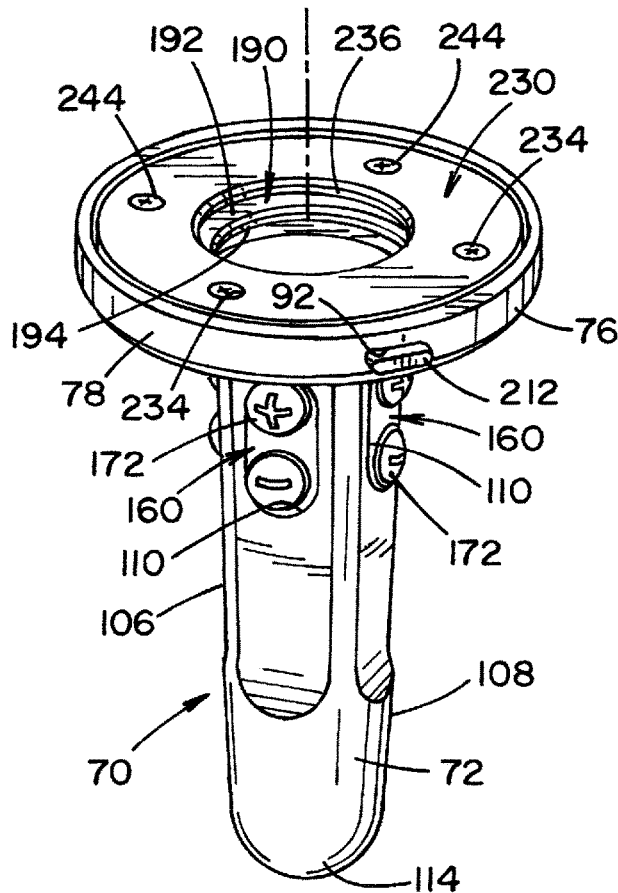
FIG. 4 is a second perspective view of the detachable handle.
Figure 7:
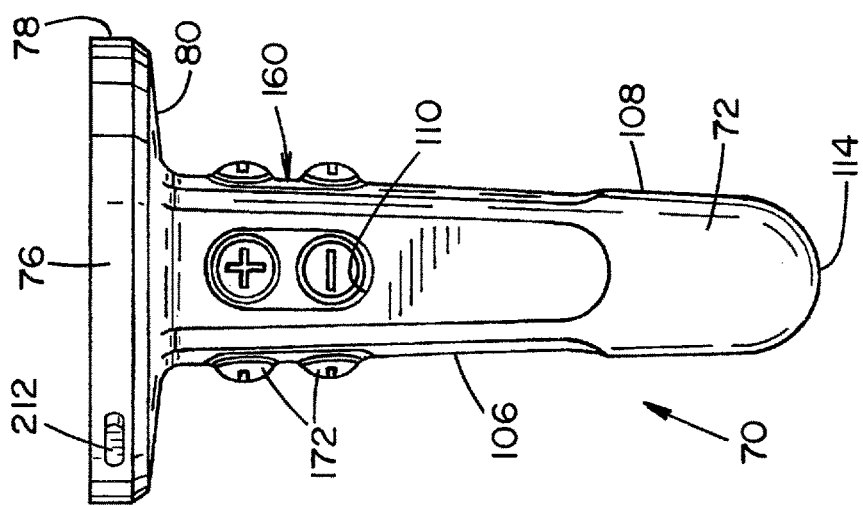
FIGS. 5-7 are side plan views of the detachable handle.
Figure 5:
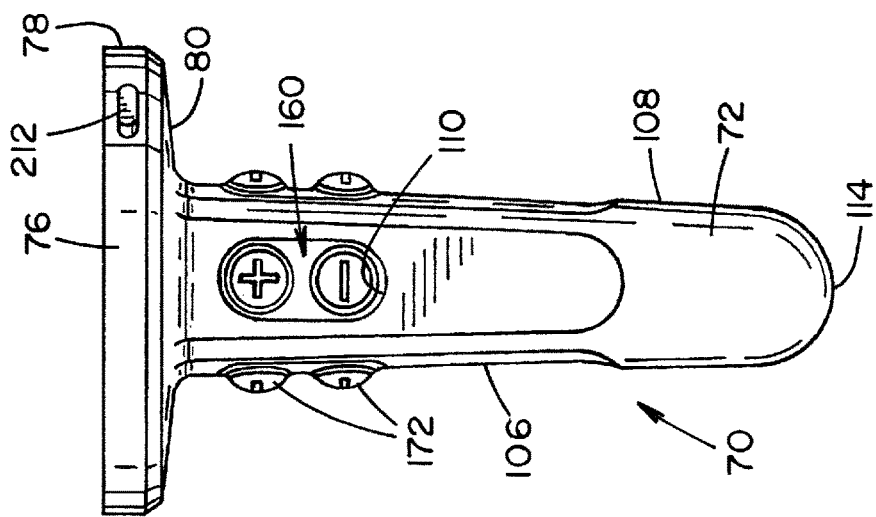
Figure 6:
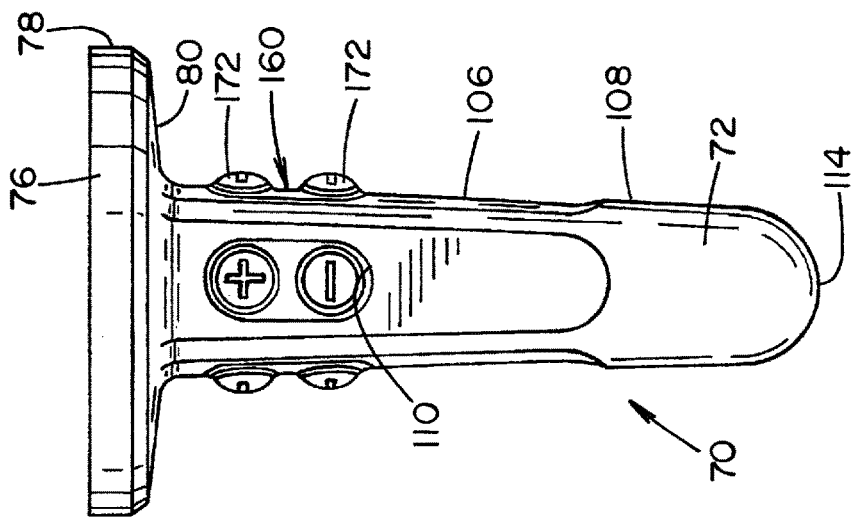

Retaining ring 230 is generally ring-shaped with a center opening 236, as best seen in FIGS. 4, 9 and 10. Retaining ring 230 includes a plurality of receptacles 232 for receiving mounting bosses 82 of outer housing 72. Each receptacle 232 includes an opening 234 dimensioned to receive fastener 244 for fixing retaining ring 230 to outer housing 72. Retaining ring 230 captures locking member 190 between retaining ring 230 and head portion 132 of inner shell 130.

According to an embodiment of the present invention, outer housing 72, inner shell 130, locking member 190 and retaining ring 230 are made of a molded plastic that is suitable for decontamination using a conventional steam sterilization process.

Base 20 of handle assembly 15 is generally comprised of a proximal section 22, a locking section 30, and a stem section 42, as best seen in FIGS. 8-12. Proximal section 22 has a front face 24 and a rear face 26, as best seen in FIG. 8. Locking section 30 includes an annular groove 32 and a frustoconical-shaped portion 34. Frustoconical-shaped portion 34 has a front face 36. Annular groove 32 is dimensioned to receive an edge portion of ring section 192 of locking member 190 located adjacent to opening 194. Detachable handle 70 is mounted to base 20 by capturing the edge portion of ring section 192 in annular groove 32. In the illustrated embodiment, stem section 42 has a plurality of side faces 44 and a front face 46. According to an embodiment of the present invention, base 20 is made of anodized aluminum. Base 20 also includes contact elements 60 that are mounted to each of the side faces 44 of base 20. Each contact element 60 has one or more tactile electrical dome switches 64 that are engaged by depressing button elements 170 of button membrane 160. Lead wires W extend from contact elements 60 through one or more channels formed in base 20 to connect with the control unit. Contact element 60 may take the form of a conventional PCB contact switching element.

It should be appreciated that detachable handle 70 may also be mechanically adapted to rotate about its axis as a means for adjusting a pattern size of the light produced by lighting unit 5.

Figure 13:
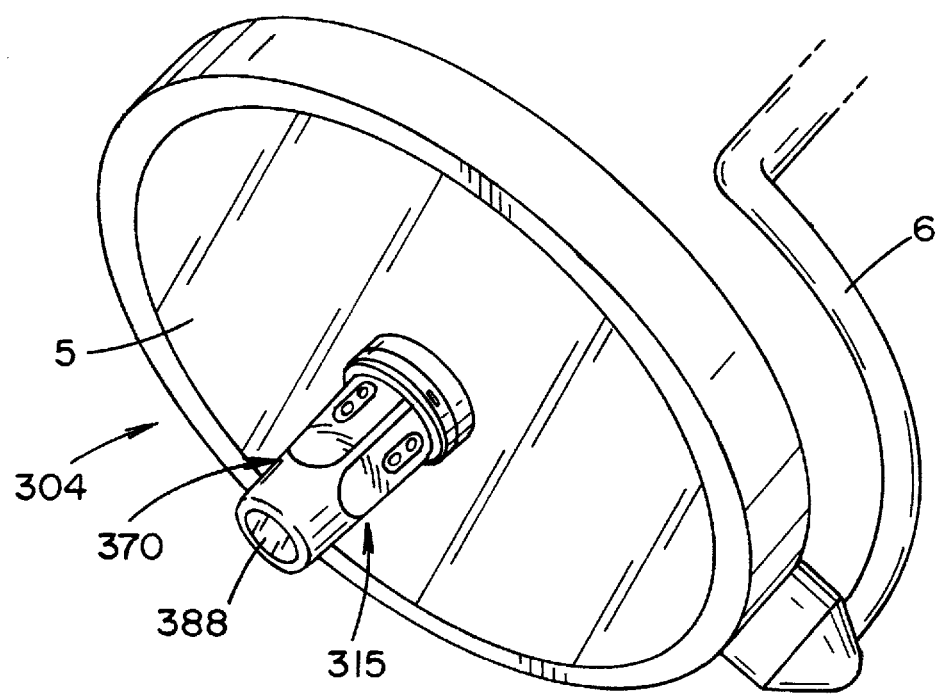
FIG. 13 is a perspective view of a lighting system including a handle assembly according to an alternative embodiment of the present invention, said handle assembly including a base and a detachable handle that also functions as a camera housing.
Figure 14:
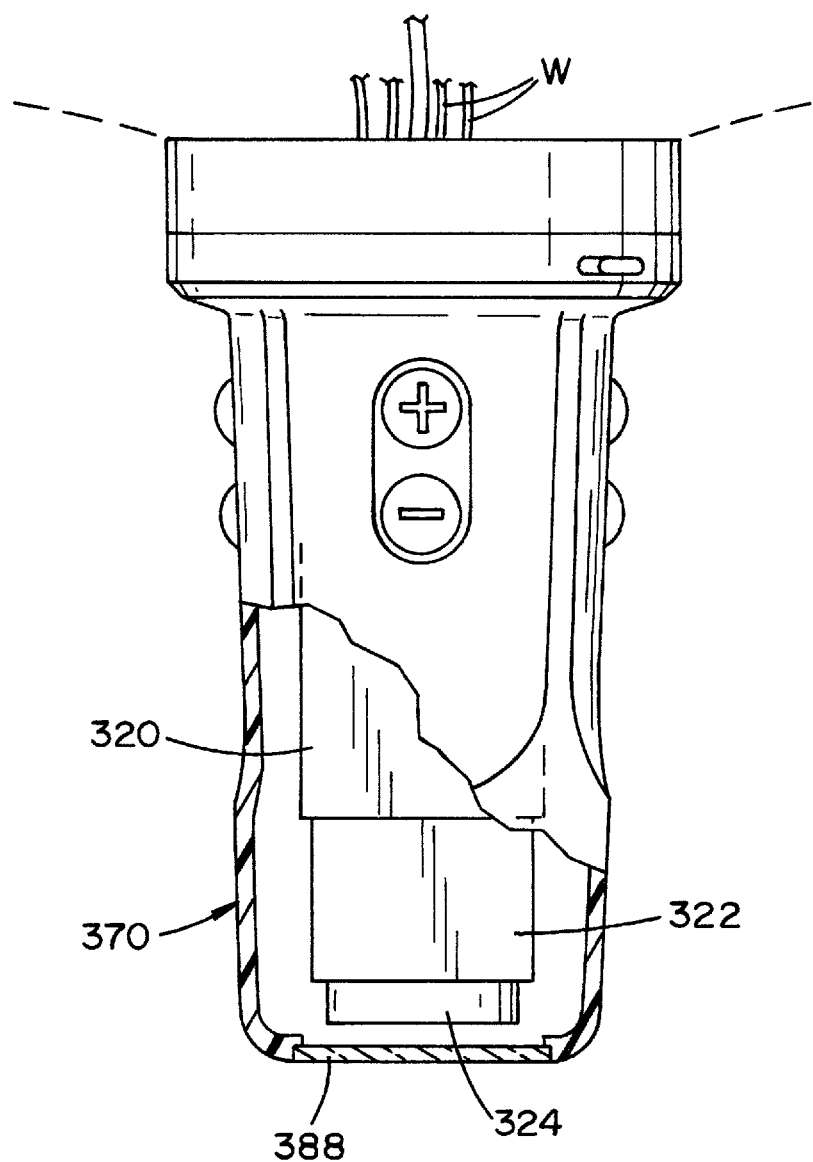
FIG. 14 shows the handle assembly of FIG. 13, with a partial sectional view of the detachable handle.

Referring now to FIGS. 13 and 14, an alternative embodiment of the present invention will be described. A lighthead 304 is comprised of a handle assembly 315 according to an alternative embodiment of the present invention. Handle assembly 315 has several components in common with handle assembly 15. In the illustrated embodiment, handle assembly 315 is generally comprised of a base 320 and a detachable handle 370 that also functions as a camera housing. Detachable handle 370 is substantially similar to detachable handle 70. However, a transparent window 388 is provided at the distal end of detachable handle 370. Base 320 is substantially similar to base 20. However, base 320 includes a camera comprised of an imaging unit 322 and a lens 324 at the distal end thereof.

Assembly and operation of handle assembly 15 will now be described. To mount detachable handle 70 to base 20, the longitudinal axis of detachable handle 70 is aligned with the longitudinal axis of base 20. Stem section 42 of base 20 is received within body portion 106, as best seen in FIG. 9. Detachable handle 70 is fixed to base 20 by engagement of locking member 190 with locking section 30 of base 20. Locking member 190 is movable from a locked position to an unlocked position by depressing release button 212. In the locked position, the edge portion of ring section 192 of locking member 190 is captured in annular groove 32 of locking section 30 of base 20. Bias member 90 is biased to apply a force that normally maintains locking member 190 in the locked position, as shown in FIGS. 9 and 10. When detachable handle 70 is mounted to base 20, engagement portions 176 of button membrane 160 are aligned with dome switches 64 of base 20, as best seen in FIG. 9. When a user depresses a contact portion 172 of button membrane 160, engagement portion 176 engages a dome switch 64 to activate an electronic control (e.g., light intensity). To dismount detachable handle 70 from base 20 release button 212 is depressed to move locking member 190 to the unlocked position, thereby allowing detachable handle 70 to be separated from base 20. Detachable handle 70 can then be decontaminated in a decontamination processing device, such as a steam sterilizer.

Handle assembly 315 assembles and operates in a similar manner as handle assembly 15. However, the button elements of detachable handle 370 may also be used for control of imaging unit 322. It should be appreciated that handle assemblies 15 and 315 may be interchangeably mountable to base 20.

The foregoing describes specific embodiments of the present invention. It should be appreciated that these embodiments are described for purposes of illustration only, and that numerous alterations and modifications may be practiced by those skilled in the art without departing from the spirit and scope of the invention. For example, it is contemplated that the detachable handle of the present invention may be adapted to incorporate additional components that are not described above, including, but not limited to, a laser, a distance sensor, etc. It is intended that all such modifications and alterations be included insofar as they come within the scope of the invention as claimed or the equivalents thereof.

Having described the invention, the following is claimed:

1. A handle assembly for a lighting system, comprising:
   a base having a stem section that includes at least one contact element mounted thereto, each contact element having one or more switches; and
   a detachable handle mountable to the base, the handle including:
      an outer housing having a head portion and a body portion, and
      a button membrane having one or more button elements accessible through an opening formed in the outer housing, each button element respectively aligned with one of said switches when the detachable handle is mounted to the base to allow engagement of the button elements with the switches.

2. The handle assembly of claim 1, wherein said base includes a locking section for locking the detachable handle to the base.

3. The handle assembly of claim 1, wherein the button membrane is mounted in the body portion.

4. The handle assembly of claim 1, wherein said detachable handle includes an inner shell having:
   a head portion dimensioned to be received by the head portion of the outer housing; and
   a body portion dimensioned to be received by the body portion of the outer housing.

5. The handle assembly of claim 2, wherein said detachable handle includes a locking member moveable between locked and unlocked positions, wherein said locked position fixes the detachable handle to said locking section of the base.

6. The handle assembly of claim 1, wherein each contact element has at least one lead wire connected to a control unit for the lighting system.

7. The handle assembly of claim 1, wherein each contact element is a PCB contact switching element.

8. The handle assembly of claim 1, wherein said button membrane is illuminated.

9. The handle assembly of claim 1, wherein said base includes an imaging unit and a lens.

10. The handle assembly of claim 1, wherein said detachable handle includes a transparent window at a distal end thereof.

11. The handle assembly of claim 1, wherein each button element includes (i) an engagement portion for engagement with one of the switches and (ii) a contact portion for user contact with the button element.

12. The handle assembly of claim 1, when said body portion includes a recess dimensioned to receive the stem section of the base.

* * * * *